(12) United States Patent
Plourde

(10) Patent No.: US 11,675,278 B2
(45) Date of Patent: Jun. 13, 2023

(54) EXHAUST GAS MONITOR FOR PHOTORESIST ADHESION CONTROL

(71) Applicant: Texas Instruments Incorporated, Dallas, TX (US)

(72) Inventor: Joseph Peter Plourde, Scarborough, ME (US)

(73) Assignee: Texas Instruments Incorporated, Dallas, TX (US)

( * ) Notice: Subject to any disclaimer, the term of this patent is extended or adjusted under 35 U.S.C. 154(b) by 0 days.

(21) Appl. No.: 17/323,767

(22) Filed: May 18, 2021

(65) Prior Publication Data

US 2022/0221801 A1 Jul. 14, 2022

Related U.S. Application Data

(60) Provisional application No. 63/137,317, filed on Jan. 14, 2021.

(51) Int. Cl.
*G03F 7/00* (2006.01)
*G01N 33/00* (2006.01)
*G03F 7/20* (2006.01)

(52) U.S. Cl.
CPC ....... *G03F 7/7085* (2013.01); *G01N 33/0047* (2013.01); *G01N 33/0054* (2013.01); *G03F 7/70825* (2013.01)

(58) Field of Classification Search
CPC ...... G03F 7/7085; G03F 7/70825; G03F 7/16; G01N 33/0047; G01N 33/0054
See application file for complete search history.

(56) References Cited

U.S. PATENT DOCUMENTS 6,650,409 B1 * 11/2003 Noguchi ............ G01N 21/9501
356/237.4
2017/0365473 A1 * 12/2017 Davis .................. H01L 21/0262

FOREIGN PATENT DOCUMENTS

| CN | 201689872 U | 12/2010 |
| WO | 9933095 A1 | 7/1999 |
| WO | 2004073049 A2 | 8/2004 |

OTHER PUBLICATIONS

Figaro Engineering Inc., TGS 2603—for detection of Odor and Air Contaminants, Sep. 2013, 2 pgs., https://www.figaro.co.jp/en/product/docs/tgs2603_product_information_rev02.pdf, accessed Mar. 13, 2021.

(Continued)

*Primary Examiner* — Hung V Nguyen
(74) *Attorney, Agent, or Firm* — Andrew R. Ralston; Frank D. Cimino

(57) ABSTRACT

An exhaust stream monitoring system for a photolithography track of an IC fabrication process comprises a reaction chamber including a housing, an inflow port and an outflow port, the housing containing a thermal plate for heating a semiconductor process wafer for a predetermined amount of time. An influent pipe coupled to the inflow port supplies a photoresist adhesion promoter in a gaseous form to the reaction chamber. An effluent pipe coupled to the outflow port is operative to remove byproducts from the reaction chamber as an exhaust stream. At least one gas sensor manifold assembly is coupled to the effluent pipe for monitoring the exhaust stream from the reaction chamber to detect presence of one or more byproducts of a reaction between the photoresist adhesion promoter and the semiconductor process wafer.

20 Claims, 8 Drawing Sheets

(56) References Cited

OTHER PUBLICATIONS

Figaro USA, Inc., TGS 826—for the Detection of Ammonia, May 2004, 3 pgs., https://www.figarosensor.com/product/docs/TGS 826 (05_04).pdf, accessed Mar. 13, 2021.
International Search Report, dated Jul. 4, 2022, 2 pages.

* cited by examiner

EXHAUST GAS MONITOR FOR PHOTORESIST ADHESION CONTROL

PRIORITY AND CROSS-REFERENCE TO RELATED APPLICATION(S)

This application claims the benefit of and priority to the following U.S. provisional patent application(s): (i) HMDS EXHAUST MONITOR FOR PHOTOLITHOGRAPHY TRACKS", Application No. 63/137,317, filed Jan. 14, 2021, in the name(s) of Joseph Peter Plourde; each of which is hereby incorporated herein by reference in its entirety.

FIELD OF THE DISCLOSURE

Disclosed implementations relate generally to the field of semiconductor fabrication, and more particularly, but not exclusively, to an exhaust gas monitor for facilitating photoresist adhesion control.

BACKGROUND

A semiconductor circuit is fabricated by using sequences of semiconductor substrate preparation, patterning, etching, metallization, etc., which may be used in various combinations to form the desired semiconductor circuit or integrated circuit in a substrate. As part of the semiconductor fabrication process, photolithography is used to delineate patterns representing particular device or circuit structures on the surface of a semiconductor wafer. This pattern is made with a photoresist, which protects the substrate underneath it from subsequent processing. The physical or electrical characteristics of the unprotected surfaces are altered by a number of subsequent process steps such as etch, deposition, ion implantation, sputtering, etc. The foregoing cycle of patterning and subsequent processing may be repeated several times until the entire device is completed.

Good adhesion of the photoresist is important to ensure the integrity of pattern transfer during photolithography. To prepare a semiconductor process wafer for better adhesion of the photoresist, a priming process using a suitable adhesion promoter is often performed. Any failure that compromises the integrity of the priming process can be costly because the resulting poor adhesion of the photoresist can cause device defects (e.g., due to failures in a subsequent etching step), which may not be detected until after many processing steps have been undertaken.

SUMMARY

In one aspect, an implementation of a system is disclosed for monitoring exhaust gases of an adhesion promotion reaction process to determine whether the reaction process is performed in a satisfactory manner. The system comprises, inter alia, a reaction chamber including a housing, an inflow port and an outflow port, the housing containing a thermal plate for heating a semiconductor process wafer at a predetermined temperature for a predetermined amount of time. An incoming or influent pipe is coupled to the inflow port for supplying a photoresist adhesion promoter in a gaseous form to the reaction chamber (e.g., hexamethyldisilazane (HMDS) vapor in a carrier gas). An effluent pipe is coupled to the outflow port for exhausting byproducts from the reaction chamber. At least one gas sensor manifold assembly coupled to the effluent pipe is provided for monitoring an exhaust stream from the reaction chamber to detect presence of one or more byproducts of a reaction between the photoresist adhesion promoter and the semiconductor wafer.

In another aspect, an implementation of a method of fabricating an integrated circuit (IC) is disclosed. The method comprises, inter alia, prior to application of a photoresist (PR) layer in a photolithography step used in fabricating the IC on a semiconductor process wafer, applying an adhesion promoter in a gaseous form to the semiconductor process wafer disposed in a reaction chamber; and monitoring an exhaust stream flowing from the reaction chamber for detecting presence of one or more byproducts of a reaction between the adhesion promoter and the semiconductor process wafer. Responsive to determining that a detected byproduct is present in the exhaust stream in a quantity above a corresponding threshold, the semiconductor process wafer may be advanced to a next stage in IC fabrication. In one variation, example process flow may involve performing, without limitation, at least one of (i) terminating subsequent processing of the semiconductor process wafer (e.g., the semiconductor process wafer is not advanced to PR application), and/or (ii) designating the semiconductor process wafer for rework or scrap.

BRIEF DESCRIPTION OF THE DRAWINGS

Implementations of the present disclosure are illustrated by way of example, and not by way of limitation, in the Figures of the accompanying drawings. It should be noted that different references to "an" or "one" implementation in this disclosure are not necessarily to the same implementation, and such references may mean at least one. Further, when a particular feature, structure, or characteristic is described in connection with an implementation, it is submitted that it is within the knowledge of one skilled in the art to effect such feature, structure, or characteristic in connection with other implementations whether or not explicitly described.

The accompanying drawings are incorporated into and form a part of the specification to illustrate one or more example implementations of the present disclosure. Various advantages and features of the disclosure will be understood from the following Detailed Description taken in connection with the appended claims and with reference to the attached drawing Figures in which:

DETAILED DESCRIPTION OF THE DRAWINGS

Figure 1:
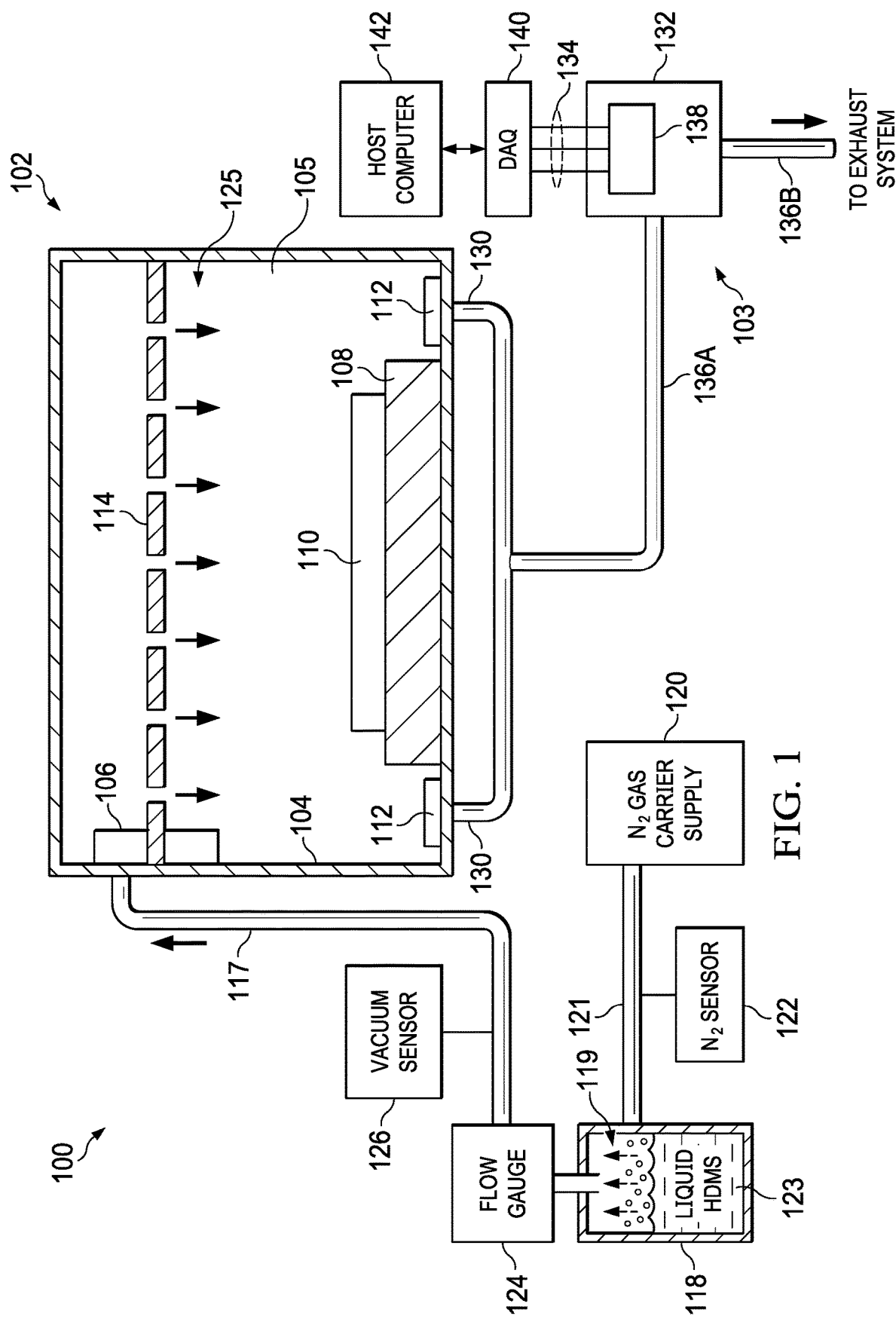
FIG. 1 depicts an example system including an exhaust gas monitoring apparatus for use in a photolithography track of an IC fabrication process according to an implementation of the disclosure.

Example embodiments of the disclosure are described with reference to the attached Figures wherein like reference numerals are generally utilized to refer to like elements. The Figures are not drawn to scale and they are provided merely to illustrate example embodiments. Numerous specific details, relationships, and methods are set forth below to provide an understanding of one or more example embodiments. However, it should be understood that some embodiments may be practiced without such specific details. In other instances, well-known circuits, subsystems, components, structures and techniques have not been shown in detail in order not to obscure the understanding of the example embodiments. Accordingly, it will be appreciated by one skilled in the art that the embodiments of the present disclosure may be practiced without such specific components.

In the following description, reference may be made to the accompanying drawings wherein certain directional terminology, such as, e.g., "upper", "lower", "top", "bottom", "left-hand", "right-hand", "front side", "backside", "vertical", "horizontal", etc., may be used with reference to the orientation of the Figures or illustrative elements thereof being described. Because components of some embodiments can be positioned in a number of different orientations, the directional terminology is used for purposes of illustration and is in no way limiting. Likewise, references to features referred to as "first", "second", etc., are not indicative of any specific order, importance, and the like, and such references may be interchanged mutatis mutandis, depending on the context, implementation, etc. Further, the features of example embodiments described herein may be combined with each other unless specifically noted otherwise.

As used herein, the term "couple" or "couples" is intended to mean either an indirect or direct conductive connection unless qualified as in "communicably coupled" which may include wireless connections. Thus, if a first device couples to a second device, that connection may be through a direct conductive connection, or through an indirect conductive connection via other devices and connections.

Referring now to the drawings and more particularly to FIG. 1, shown therein is an example system 100 for use in a photolithography track of an integrated circuit (IC) fabrication process wherein an exhaust monitoring apparatus 103 may be provided according to an implementation of the disclosure. As will be set forth further below, system 100 may be deployed in any IC fabrication flow wherein an adhesion promoter (AP) material is applied to a semiconductor process wafer prior to a photoresist (PR) step in order to improve photoresist adhesion at any process stage that requires photolithographic patterning (e.g., during any of the front-end-of-line (FEOL) or back-end-of-line (BEOL) stages before a final passivation layer is added to the wafer).

Without limitation, example system 100 and associated exhaust monitoring apparatus 103 will be described according to an implementation wherein a gaseous photoresist adhesion promoter, e.g., hexamethyldisilazane (HMDS) belonging to a class of hexa-alkyldisilazane promoters, is applied to the semiconductor process wafer comprising a silicon substrate in a reaction chamber for facilitating a reaction process that primes the surface for enhancing the adhesion of a subsequent PR layer. Depending on the substrate material and associated process layers thereon, the HMDS reaction process may be effectuated to release certain byproducts indicative of a reliable surface chemistry that promotes PR adhesion, wherein one or more specific byproducts (also referred to as benchmark byproducts) may be monitored to determine whether the reaction process for effectuating HMDS treatment of the process wafer has been performed satisfactorily or otherwise (e.g., compromised for some reason).

In one arrangement, system 100 comprises a reaction chamber 102 including a housing 104, one or more inflow ports 106 and one or more outflow ports 112, wherein a thermal plate 108 may be disposed in an interior 105 of housing 104 that is equipped and instrumented for subjecting at least one semiconductor process wafer 110 to a set of process conditions, e.g., at predetermined temperatures, vacuum pressures, timing ranges, etc., which may be dependent on the semiconductor wafer substrate composition, particular photolithography layer, type and chemistry of the photoresist to be used, inter alia. For purposes of the present disclosure, semiconductor process wafers 110 may also be referred to as semiconductor wafers, process wafers, work-in-progress (WIP) wafers, or the like without loss of generality, which may be contained in suitable holder, tray, carrier, or wafer conveyor (not specifically shown in FIG. 1), wherein process wafer(s) 100 may be placed in horizontal, vertical or other orientation when disposed in housing 104 for processing. Depending on implementation, reaction chamber 102 may be configured to provide both vacuum baking and vapor priming, which may be used to create a heated vacuum environment in interior 105 for dehydration and vapor priming of the semiconductor process wafer in a single cycle. Accordingly, reaction chamber 102 may also be referred to by various informal and formal terms somewhat synonymously in some arrangements, e.g., "bake oven", "vapor deposition chamber", or other terms of similar import.

In one arrangement, a gas (e.g., nitrogen) may be used as a carrier for carrying HMDS in gaseous form via one or more piping or conduit systems associated with reaction chamber 102. By way of illustration, a nitrogen gas supply canister 120 is operative to supply $N_2$ gas to a tank or container 118 containing liquid HMDS 123 via a conduit portion 121, which may be monitored by an $N_2$ sensor 122. In one arrangement, HMDS container 118 may be pressurized with $N_2$ gas. Depending on implementation, $N_2$ gas is allowed to flow over the surface of or bubble through liquid HMDS 123 during processing to create an HMDS-rich vapor or aerosol admixture 119, which may be piped via conduit portions 116, 117 to reaction chamber 102. A flow gauge 124 and a vacuum sensor 126 may be coupled to conduit portions 116, 117 at suitable locations for monitoring flow conditions of HMDS vapor and $N_2$ gas admixture 119, wherein at least conduit portion 117 may be deployed as an influent pipe coupled to inflow port 106 of housing 104.

In one arrangement, housing 104 of reaction chamber 102 may include one or more perforated applicators 114 (informally referred to as "shower heads") coupled to or otherwise associated with inflow port(s) 106 for evenly distributing the adhesion promoter admixture as flow 125 over semiconductor process wafer 110 disposed in housing 104, which facilitates substantially uniform diffusion of the gaseous adhesion promoter material onto the wafer surface. Under appropriate process conditions, one or more chemical and/or surface reactions involving HMDS and several reactants (e.g., including but not limited to surface $H_2O$, interior ambient $H_2O$, oxygen, various ceramics and oxides, metal/non-metal surface layers depending on topography, wafer substrate material, etc.), collectively referred to as a reaction process, may be initiated in reaction chamber 102 for causing a suitable surface treatment of the semiconductor wafers. HMDS, as a silane coupling agent, is operative to react with the surface of metals and ceramics to form hydrophilic trimethylsilanol (TMSiOH) on the surface, which facilitates easier coating of a semiconductor wafer surface with photoresist at a subsequent stage. HMDS is also operative to react with ambient moisture and gradually convert to ammonia ($NH_3$) and methyl silanol.

Various byproducts resulting from the foregoing reaction process may therefore comprise at least one of ammonia, tri-methylamine and one or more volatile organic compounds (VOCs), which may be removed as an exhaust stream from reaction chamber 102 via one or more effluent pipes 130 coupled to housing 104 at corresponding outflow ports 112. At least one gas sensor manifold assembly 132 containing an appropriate gas sensor 138 (e.g., ammonia sensor, tri-methylamine sensor, VOC sensor, etc.) may be coupled to effluent pipe 130 as part of exhaust monitoring apparatus 103 for monitoring the exhaust stream to detect the presence of one or more benchmark byproducts (depending on which byproduct(s) is(are) selected for measurement) in order to facilitate a determination of whether the HMDS reaction process has been performed satisfactorily or otherwise (e.g., due to any leaks or failures resulting in a reduction or elimination of HMDS vapor being carried into reaction chamber 102, etc.). An electrical interface 134 of sensor 138 may be coupled to a data acquisition (DAQ) unit 140 for collecting sensor data and transmitting the data to a host computer 142 using any known or heretofore unknown data collection/transmission protocols in conjunction with suitable wireless and/or wireline communications technologies and infrastructures, wherein the data may be processed for generating suitable reports, notifications/alarms, and the like (generally referred to as "actionable process intelligence") regarding the state of the HMDS reaction process. Depending on implementation, host computer 142 may be deployed as a local or remote host, or at a cloud-based data center associated with an IC fabrication facility.

In one arrangement, process conditions for effectuating an example HMDS reaction process in reaction chamber 102 may comprise heating semiconductor wafer(s) 110 disposed in housing 104 at a temperature ranging approximately between 70° C. and 150° C. for about a few seconds to several seconds (e.g., 5 to 30 seconds) at an interior ambient pressure of about 1 Torr. Depending on a particular IC fabrication flow, an example HMDS processing stage may include other steps, procedures or operations in some additional and/or alternative arrangements. For example, a purge cycle may be employed to purge ambient gases from interior 105 of reaction chamber 102 prior to supplying HMDS. In a pump and purge arrangement, a series of vacuum and nitrogen applications may be provided in order to remove ambient oxygen and moisture from interior 105. Pre-heated nitrogen may be supplied to heat the semiconductor wafers to a desired process temperature. In some arrangements, reaction chamber 102 may be evacuated to low pressure and refilled with pure nitrogen several times to substantially completely remove the ambient moisture. Prior to supplying HMDS and nitrogen admixture, ambient pressure in reaction chamber 102 may be pumped down to a suitable pressure (e.g., about 1 Torr) depending on tooling conditions. HMDS and nitrogen admixture may be supplied in a diffusive manner for a designated amount of time for effectuating the HMDS reaction process as exemplified above. Excess HMDS and gaseous byproducts may be evacuated as exhaust stream, whereupon additional vacuum/nitrogen cycles may be employed to ensure complete removal of the byproducts from reaction chamber 102.

Continuing to refer to FIG. 1, gas sensor manifold assembly 132 may be coupled to effluent pipe 130 at a suitable location before the exhaust stream is delivered to an exhaust system associated with reaction chamber tooling (not specifically shown in FIG. 1) to safely remove the gaseous byproducts of the HMDS reaction process for proper environmental disposal. Depending on implementation, an example system may comprise an active exhaust system (e.g., a pump-based mechanism) or a passive exhaust system (e.g., a passive ventilation system). In one arrangement, gas sensor manifold assembly 132 may be axially disposed between a first portion 136A and a second portion 136B of effluent pipe 130 such that sensor 138 disposed in manifold assembly 132 has unimpeded access to the gaseous exhaust stream flowing through effluent pipe 131 as will be set forth further below in additional detail.

Figure 2A:
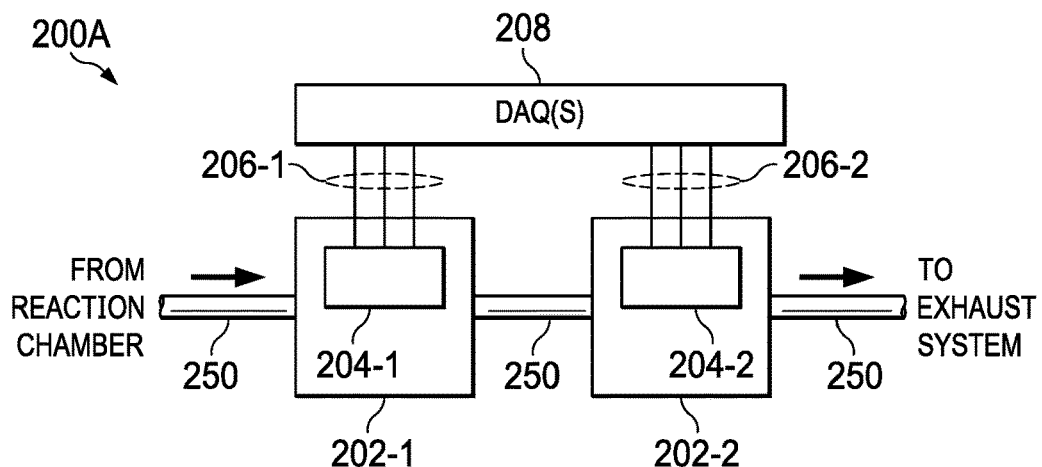
FIGS. 2A and 2B depict example arrangements of multiple gas sensor manifold assemblies that may be deployed for monitoring exhaust gas byproducts according to an implementation of the disclosure.
Figure 2B:
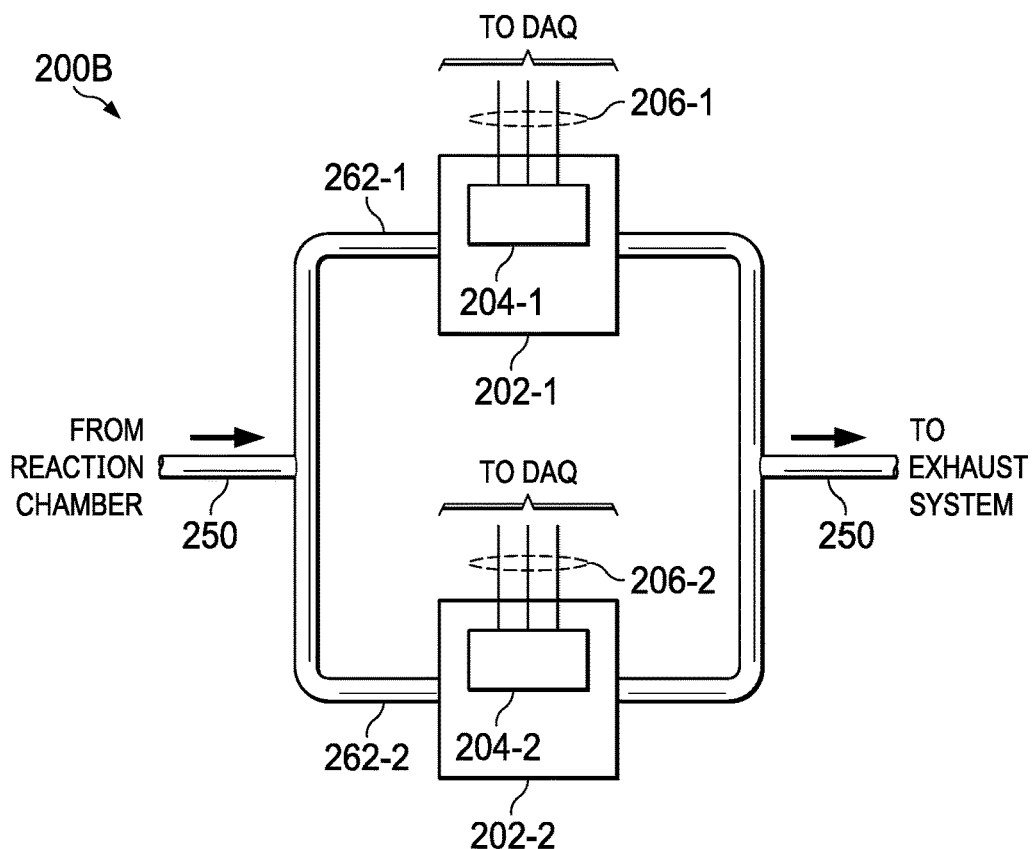

In some arrangements, exhaust monitoring apparatus 103 may include multiple gas sensor manifold assemblies that may be coupled to effluent pipe 130 at various locations, wherein each gas sensor manifold assembly may be configured to include a sensor operative to detect and measure a particular byproduct in the exhaust stream. As previously noted, such sensors may comprise one or more ammonia sensors, one or more tri-methylamine sensors, one or more VOC sensors, etc., in any combination thereof, wherein respective electrical interfaces of the sensors may be coupled to one or more DAQ units. FIGS. 2A and 2B depict example arrangements of multiple gas sensor manifold assemblies that may be deployed according to an implementation of the disclosure. Arrangement 200A of FIG. 2A is illustrative of a deployment scenario where two or more gas sensor manifold assemblies 202-1, 202-2, each containing a respective sensor 204-1, 204-2, are disposed in a series formation along an effluent pipe portion 250 emanating from a reaction chamber. Respective electrical interfaces 206-1, 206-2 of sensors 204-1, 204-2 are operative to be coupled to a separate DAQ, respectively, or a single DAQ operative to support multiple sensors, which is(are) collectively shown as DAQ(s) 208. Arrangement 200B of FIG. 2B is illustrative of a deployment scenario where multiple gas sensor manifold assemblies 202-1, 202-2, are disposed in a parallel formation along respective effluent pipe portions 262-1, 262-2 of effluent pipe portion 250 emanating from a reaction chamber. Effluent pipe portion 250 may be branched into multiple parallel pipe portions, e.g., portions 262-1, 260-2 operative to effectuate parallel exhaust stream flows, which may join as a single pipe portion before the exhaust stream is transported to an exhaust system. Similar to arrangement 200A of FIG. 2A, respective electrical interfaces 206-1, 206-2 of sensors 204-1, 204-2 may be coupled to a separate DAQ, respectively, or a single DAQ operative to support multiple sensors. An example deployment scenario may include any number of arrangements 200A of FIG. 2A, arrangements 200B of FIG. 2B, and/or any variations and combinations thereof, wherein multiple gas sensor manifold assemblies 202-1, 202-2 may include sensors from the same class of sensors or from a different class (e.g., any combination of ammonia sensors, tri-methylamine sensors, and/or VOC sensors, and the like).

In general, an example gas sensor manifold assembly may be constructed from any suitable materials (e.g., stainless steel) that can withstand the harsh chemical, physical and other environmental conditions of an IC fabrication line, particularly in relation to the tooling used in PR adhesion promoter processing. In one arrangement, an example sensor manifold assembly may be deployed as a customizable mounting block configured to couple to a reaction chamber's effluent pipe portion at any suitable location that allows a gas sensor to be safely placed in the path of an exhaust stream without leaks, etc. Accordingly, a mounting block of the present disclosure may be advantageously configured to ensure vacuum system integrity of the reaction chamber while affording robust protection of the gas sensor(s) placed in the effluent pipes associated therewith. Further, a customizable housing design of mounting blocks is operative to facilitate the accommodation of any commercially available gas/vapor sensors and/or custom-built sensors in a variety of deployment scenarios for purposes of the present disclosure. In one arrangement, example gas sensor manifold assemblies may be constructed and/or assembled as a single modular unit that may be installed in any style or type of reaction chamber equipment or tool systems, wherein appropriate inlet and outlet couplings or ports may be provided in the mounting block for mounting the modular unit in axial alignment with an exhaust effluent pipe portion. In one implementation, an example gas sensor manifold assembly may comprise a mounting block (also referred to as a housing block) having a suitable receptacle or spacing designed to house TGS 2603 series tri-methylamine sensors and TGS 826 ammonia sensors from Figaro USA Inc. and affiliated companies, although gas sensors from various sources may also be used according to some additional and/or alternative embodiments.

Figure 3:
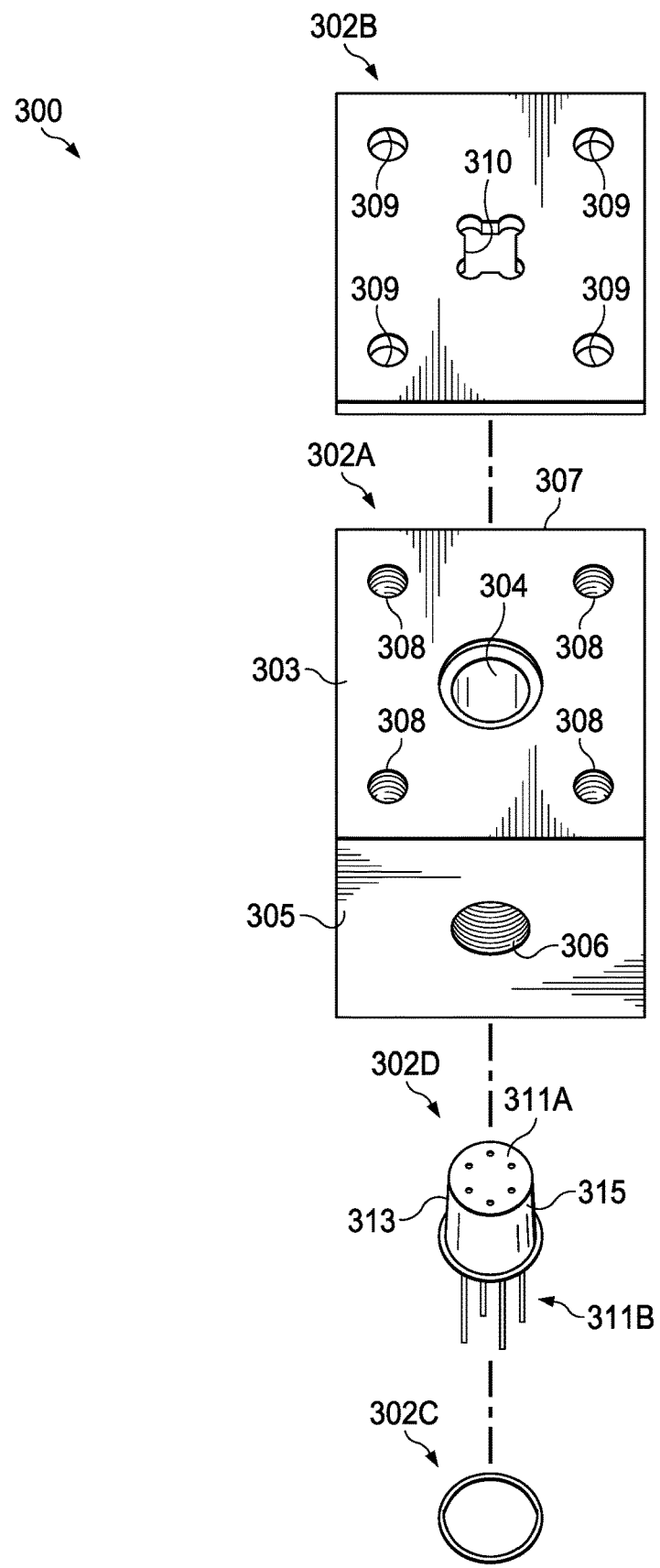
FIG. 3 depicts various components of a gas sensor manifold assembly that may be deployed for monitoring a tri-methylamine byproduct in an exhaust stream according to an implementation of the disclosure.

FIG. 3 depicts various components of a tri-methylamine sensor manifold assembly 300 that may be provided as modular unit according to an implementation of the disclosure for deployment in an example exhaust gas monitoring apparatus of FIG. 1. In one arrangement, assembly 300 includes a housing block 302A having a receptacle side 303 with a chamber or receptacle 304 contoured to accommodate tri-methylamine sensor 302D, wherein a cover plate 302B having an aperture 310 for exposing sensor 302D to external circuitry or wiring (e.g., for data acquisition) may be rigidly coupled to housing block 302A using a variety of mechanical coupling mechanisms, e.g., screws, fasteners, bolts, etc. By way of illustration, a plurality of threaded holes 308 may be provided in receptacle side 303 of housing block 302A, which align with a corresponding plurality of threaded through holes 309 of cover plate 302B for facilitating rigid mechanical coupling. Sensor 302D may comprise a first body portion 313 having a sensing portion 311A and a second body portion 315 having an electrical interface portion 311B. An O-ring seal 302C sized to seal aperture 310 of cover plate 302B may be disposed around second body portion 315 proximate to sensor 302D, e.g., proximate to electrical interface portion 311B of sensor 302D, such that O-ring seal 302C is compressed between housing block 302A and cover plate 302B when housing block 302A is rigidly coupled to cover plate 302B and sensor 302D is situated in receptacle 304 with electrical interface portion 311B exposed to external wiring/circuitry.

To provide coupling with a reaction chamber's effluent pipe and facilitate the passage of exhaust gas stream through housing block 302A for sensing, a pair of orifices having a continuous hollow spacing therebetween may be provided in housing block 302A, wherein a portion of the sensor receptacle 304 may be configured such that it opens into the hollow spacing (not specifically shown in FIG. 3), thereby allowing sensing portion 311A of sensor 302D to protrude into the hollow spacing for contacting with or immersing in the exhaust gas stream. By way of illustration, an orifice 306 is shown in a first side 305 of housing block 302A as exemplified in the 3D view thereof depicted in FIG. 3. A second orifice (not shown in FIG. 3) may be provided in a second side 307 of housing block 302A or in the same side as side 305 so long as a continuous hollow spacing (i.e., spatial continuity) may be accommodated (e.g., as a U-shaped, horse-shoe-shaped, etc., with both orifices on the same side of housing block 302A) and receptacle 304 may be contoured to have an opening that allows sensing portion 311A to contact the exhaust gas stream without obstruction. In one arrangement, an incoming effluent pipe portion may be coupled to one orifice (e.g., which referred to as an input orifice) and an outgoing effluent pipe portion may be coupled to the other orifice (e.g., which may be referred to as an output orifice) for passing the exhaust gas stream therebetween. In one arrangement, input and output orifices as well as corresponding incoming and outgoing effluent pipe portions may be thread-fitted using appropriate sealing, although skilled artisans will recognize that mechanical coupling between respective orifices and corresponding effluent pipe portions may be effectuated in a number of variations.

Figure 4:
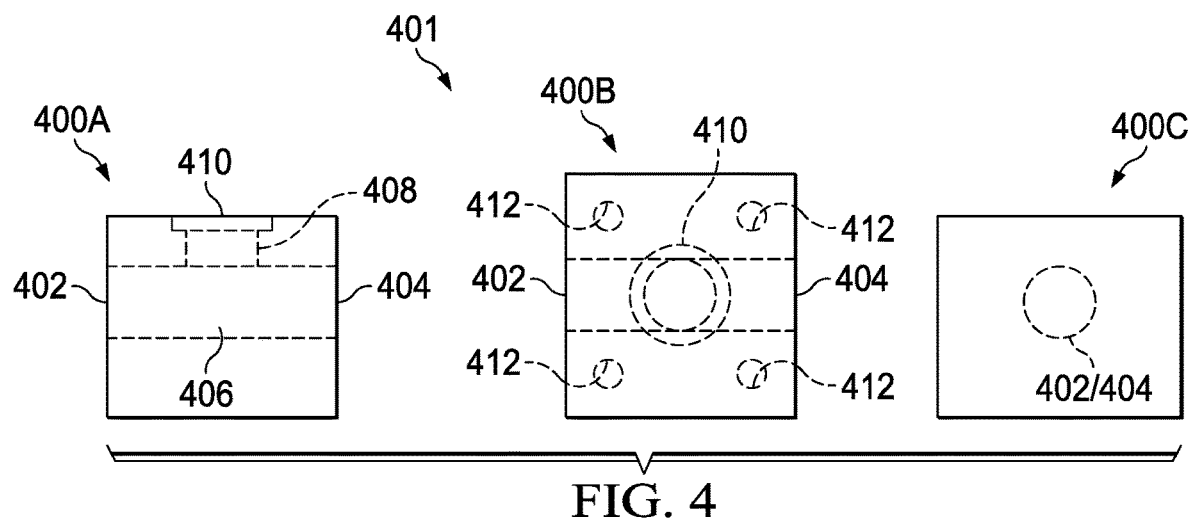
FIGS. 4 and 5 depict various views of a housing block and a cover plate of a tri-methylamine sensor manifold assembly according to an implementation of the disclosure.
Figure 5:
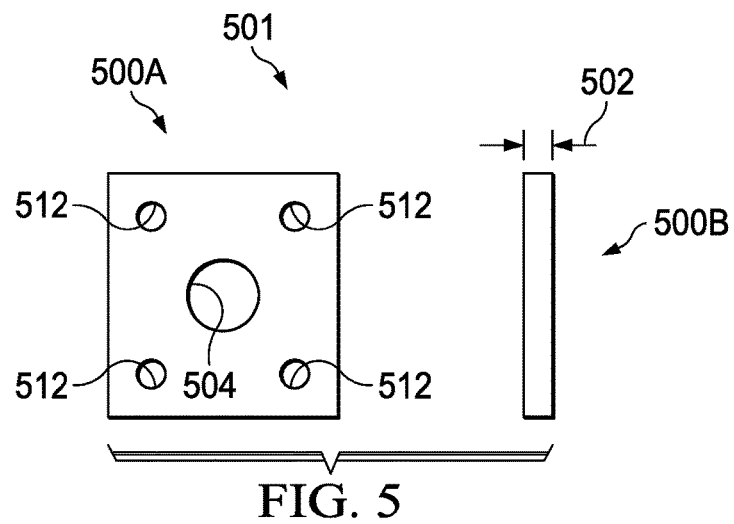

FIGS. 4 and 5 depict various views of a housing block and a cover plate of an example 3D representation of a tri-methylamine sensor manifold assembly, e.g., assembly 300 of FIG. 3, which illustrate additional details according to an implementation of the disclosure. FIG. 4 illustrates a front elevation view 400A, a top plan view 400B and a side elevation view 400C of a housing block generally shown at reference numeral 401, wherein orifices 402, 404 are joined with a tubular spacing 406 therebetween. A receptacle portion 408 of receptacle 410 opens into tubular spacing 406 to provide spatial continuity therewith. A plurality of holes 412 are shown in top plan view 400B of housing block 401 for facilitating mechanical coupling with a cover plate as described above, wherein holes 412 may be positioned away from sensor receptacle 410. FIG. 5 illustrates a top plan view 500A and a side elevation view 500B of a cover plate 501 having a thickness 502. An aperture 504 formed through cover plate 501 may be sized and shaped such that an electrical interface portion of the tri-methylamine sensor has access to outside electronics while facilitating a tight enclosure with receptacle 410 of housing block 401 when mated therewith, wherein a sealing device such as, e.g., an O-ring seal, gasket, or washer, etc., may be employed for ensuring vacuum integrity. Cover plate 501 may be provided with a plurality of through holes 512 that align with corresponding holes 412 of housing block 401, e.g., as shown in top plan view 500A of cover plate 501, for facilitating rigid mechanical coupling with housing block 401 as previously noted.

Figure 6:
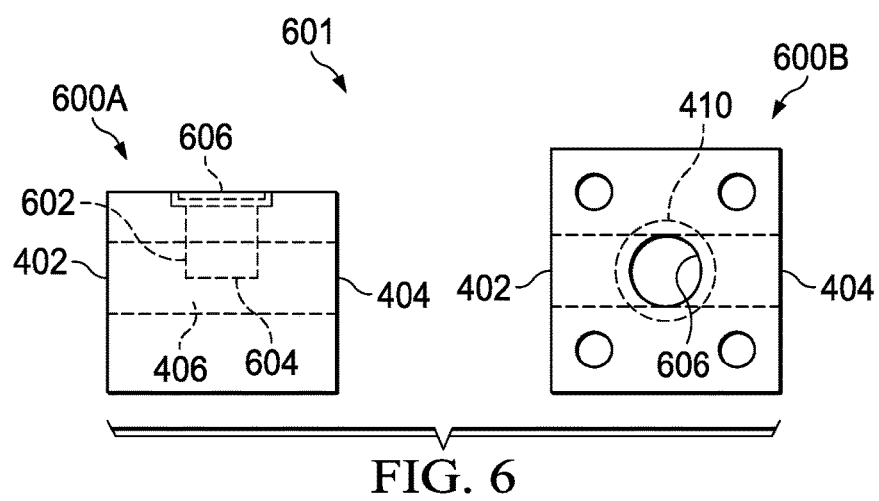
FIG. 6 depicts various views of an assembled tri-methylamine sensor manifold assembly according to an implementation of the disclosure.

FIG. 6 depicts a front elevation view 600A and a top plan view 600B of an assembled tri-methylamine sensor manifold 601 according to an implementation of the disclosure, wherein housing block 401 and cover plate 501 are assembled as a modular unit. A tri-methylamine sensor 602 is situated in receptacle 410 such that a sensing portion 604 protrudes or otherwise extends into hollow tubular spacing 406 extending between orifice 402 and orifice 404 whereas electrical interface portion 606 (shown without associated electrical connectors in this FIG.) of sensor 602 is exposed to facilitate external electrical connectivity. Depending on whether an incoming effluent pipe portion or outgoing effluent pipe portion is connected, either orifice 402, 404 may operate as an inflow port or outflow port.

Figure 11:
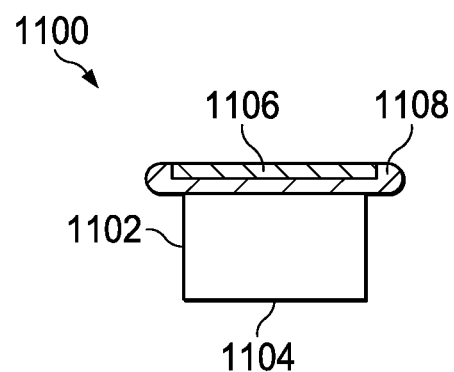
FIG. 11 depicts an example seal arrangement for a trimethylamine sensor manifold assembly according to an implementation of the disclosure.

Turning to FIG. 11, depicted therein is an example seal arrangement 1100 such as an O-ring seal for a tri-methylamine sensor manifold assembly of FIG. 3 according to an implementation of the disclosure. A tri-methylamine sensor 1102 is illustrated with a sensing portion 1104 and an electrical interface portion 1106 (wherein electrical connectors or pins are not specifically shown). An O-ring seal 1108 is disposed around sensor 1102 proximate to electrical sensing portion 1106 for providing tight seal in a modular manifold assembly as set forth above in detail.

Figure 7:
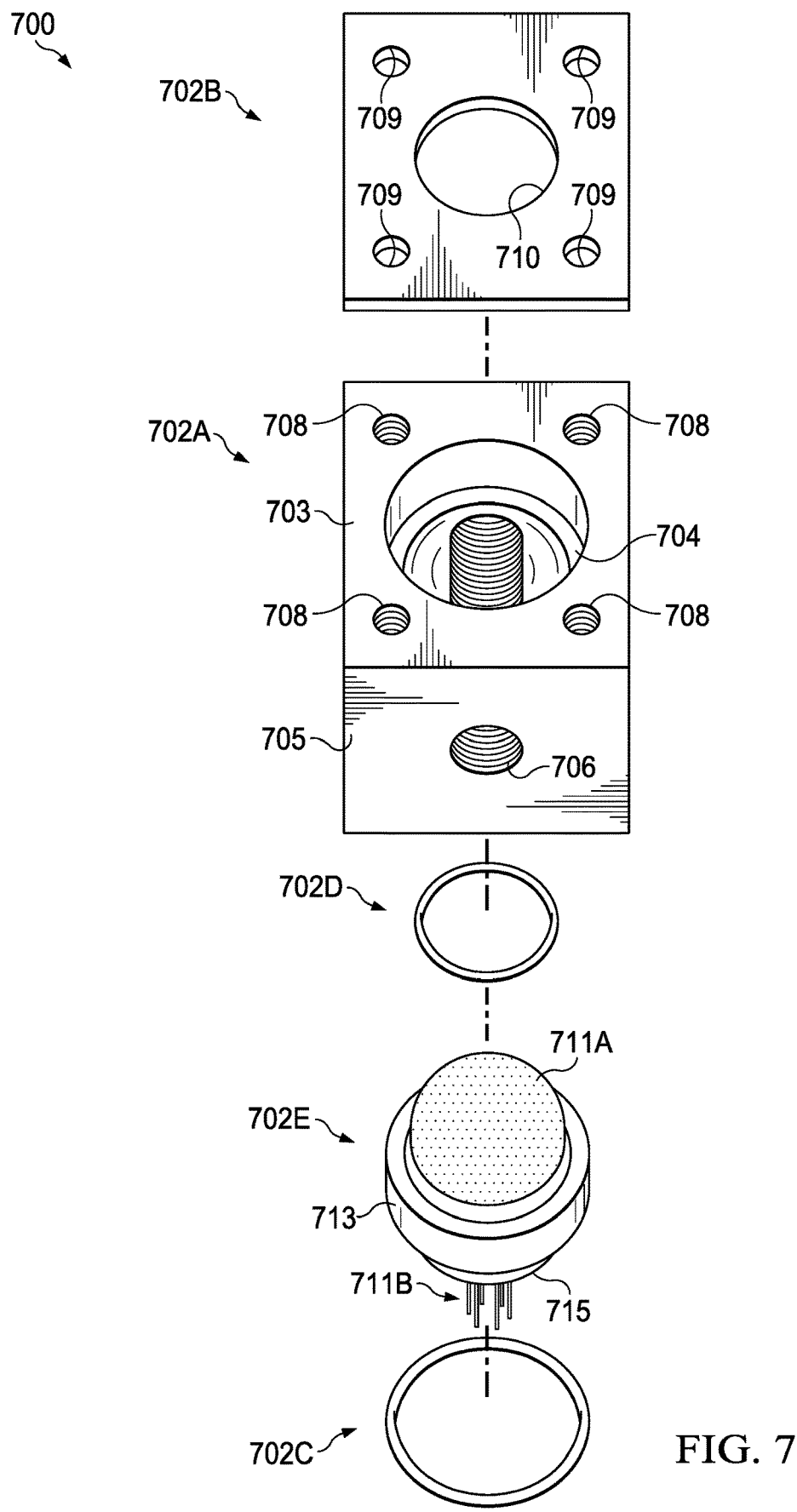
FIG. 7 depicts various components of a gas sensor manifold assembly that may be deployed for monitoring an ammonia byproduct in an exhaust stream according to an implementation of the disclosure.

FIG. 7 depicts various components of an ammonia sensor manifold assembly 700 that may be provided as modular unit according to an implementation of the disclosure for deployment in an example exhaust gas monitoring apparatus of FIG. 1. Similar to tri-methylamine sensor manifold assembly 300 of FIG. 3 above, assembly 700 includes a housing block 702A having a receptacle side 703 with a chamber or receptacle 704 contoured to accommodate an ammonia sensor 702E, which may have a different form factor than a tri-methylamine sensor. Because of the sensor form factor differences, a sensor receptacle 704 of housing block 702A may be dimensioned, shaped and/or configured differently from that of housing block 302A. Further, to ensure vacuum integrity in view of the differently shaped ammonia sensor, sealing may require more than one sealing device. Apart from the foregoing differences, ammonia sensor manifold assembly 700 may be constructed as a single modular unit in a manner substantially similar to that of tri-methylamine sensor manifold assembly 300. Accordingly, the description set forth above with respect to FIG. 3 is also generally applicable to FIG. 7, mutatis mutandis.

Ammonia sensor 702E may comprise a first body portion 713 having a sensing portion 711A and a second body portion 715 having an electrical interface portion 711B. Sensor receptacle 704 of housing block 702A may be shaped such that a receptacle portion (not specifically shown in FIG. 7), may open into a hollow spacing extending between an input orifice and an output orifice, which may be disposed on two different sides or the same side of housing block 702A for coupling with respective effluent pipe portions. By way of illustration, only one orifice 706 formed in a first side 705 is exemplified in the 3D representation of housing block 702A. A plurality of holes 708 formed in receptacle side 703 containing sensor receptacle 704 are aligned with a corresponding plurality of through holes 709 formed in cover plate 700B for facilitating rigid mechanical coupling therewith after ammonia sensor 702E is situated in receptacle 704 such that sensing portion 711A is extended into the hollow spacing formed in housing block 702A and electrical interface portion 711B is exposed to the external world via an aperture 710 of cover plate 700B for facilitating electrical connectivity with a DAQ and related circuitry.

In one arrangement, a double seal arrangement may be provided in order to ensure vacuum integrity of the tooling system, wherein a first O-ring seal 702C disposed around first body portion 713 of sensor 702E for sealing the receptacle portion opening into the hollow spacing and a second O-ring seal 702D is disposed around second body portion 715 proximate to electrical interface portion 711B for sealing a mechanical interface involving second body portion 715 and aperture 710 of cover plate 700B.

Figure 8:
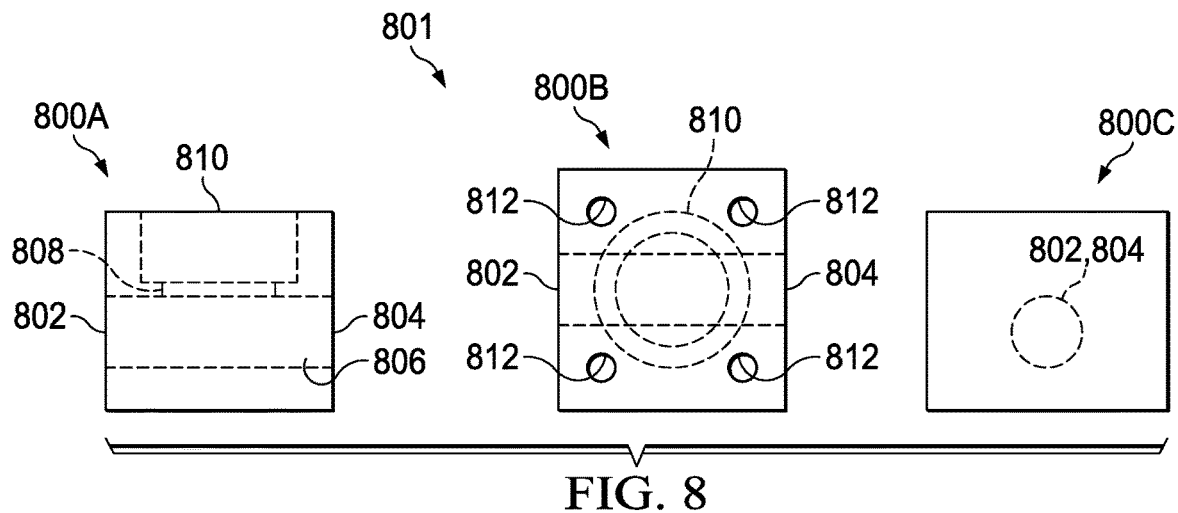
FIGS. 8 and 9 depict various views of a housing block and a cover plate of an ammonia sensor manifold assembly according to an implementation of the disclosure.
Figure 9:
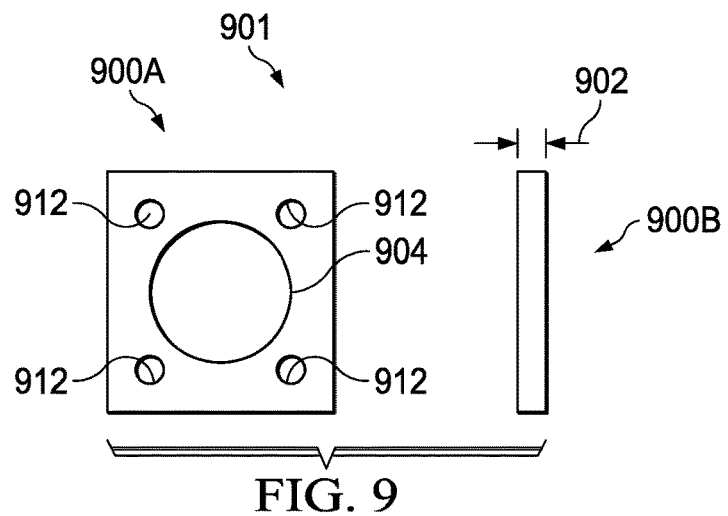

FIGS. 8 and 9 depict various views of a housing block and a cover plate of an example 3D representation of an ammonia sensor manifold assembly, e.g., assembly 700 of FIG. 7, which illustrate additional details according to an implementation of the disclosure. FIG. 8 illustrates a front elevation view 800A, a top plan view 800B and a side elevation view 800C of a housing block generally shown at reference numeral 801, wherein orifices 802, 804 are joined with a tubular spacing 806 therebetween. A receptacle portion 808 of receptacle 810 opens into tubular spacing 806, providing spatial continuity therewith. A plurality of holes 812 are shown in top plan view 800B of housing block 801 for facilitating mechanical coupling with a cover plate as previously described. FIG. 9 illustrates a top plan view 900A and a side elevation view 900B of a cover plate 901 having a thickness 902. An aperture 904 formed in cover plate 901 may be sized and shaped such that an electrical interface portion of the ammonia sensor has access to outside electronics while facilitating a tight enclosure with receptacle 810 of housing block 801 when mated therewith, wherein a sealing device such as, e.g., an O-ring seal, gasket, or washer, etc., may be employed for ensuring vacuum integrity. Further, receptacle 810 may be contoured proximate to receptacle portion 808 such that another sealing device (e.g., selected from O-ring seals, gaskets, washers, etc.) may be disposed for providing a tight seal between receptacle portion 808 and a sensing portion of the sensor. As previously noted, cover plate 901 may be provided with a plurality of through holes 912 that align with corresponding holes 812 formed in housing block 801, e.g., as shown in top plan view 900A of cover plate 901, for facilitating rigid coupling with housing block 801.

Figure 10:
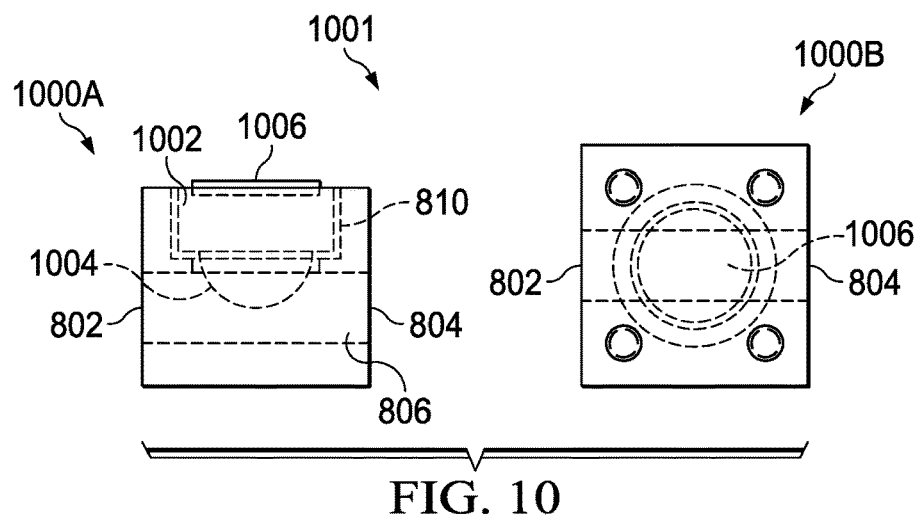
FIG. 10 depicts various views of an assembled ammonia sensor manifold assembly according to an implementation of the disclosure.

FIG. 10 depicts a front elevation view 1000A and a top plan view 1000B of an assembled ammonia sensor manifold 1001 according to an implementation of the disclosure, wherein housing block 801 and cover plate 901 are assembled as a modular unit. An ammonia sensor 1002 is situated in receptacle 810 such that a sensing portion 1004 protrudes into hollow tubular spacing 806 extending between orifice 802 and orifice 804 whereas an electrical interface portion 1006 (shown without associated electrical connectors in this FIG.) of sensor 1002 is exposed to facilitate external electrical connectivity. Depending on whether an incoming effluent pipe portion or outgoing effluent pipe portion is connected, either orifice 802, 804 may operate as an inflow port or outflow port similar to the tri-methylamine sensor manifold 1001 arrangement shown FIG. 6.

Figure 12:
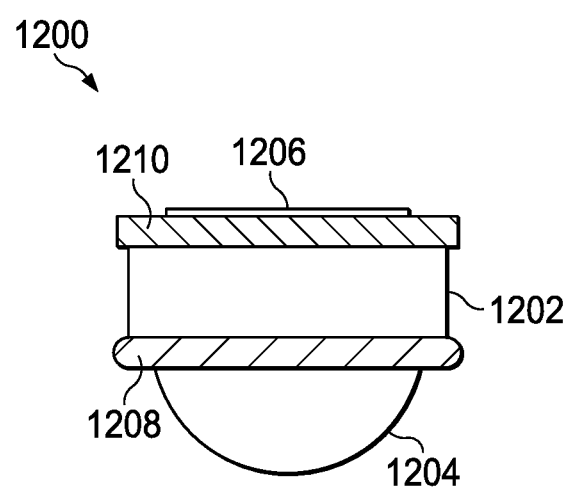
FIG. 12 depicts an example seal arrangement for an ammonia sensor manifold assembly according to an implementation of the disclosure.

Turning to FIG. 12, depicted therein is an example seal arrangement 1200 for an ammonia sensor manifold assembly of FIG. 7 according to an implementation of the disclosure. An ammonia sensor 1202 is illustrated with a sensing portion 1204 and an electrical interface portion 1206 (wherein electrical connectors or pins are not specifically shown). A first O-ring seal 1208 is disposed around a body portion of sensor 1202 proximate to sensing portion 1204 and a second O-ring seal 1210 is disposed around a body portion of sensor 1202 proximate to electrical sensing portion 1206 for providing tight seal in a modular manifold assembly as set forth above in detail.

With respect to data acquisition and processing of sensor data, various arrangements may be deployed that generally involve sensor interface wiring, signal interconnect wiring, one or more analog/digital DAQ units, sensor power supply systems, and one or more optional USB hubs (e.g., for communicating with a remote host), etc., regardless of the type or class of sensors used or whether the sensors have different electrical interface portions. Whereas example data acquisition and processing systems may have similar configurations and arrangements, specific implementations may vary based on, e.g., electrical characteristics of the sensors, sensing principles, electrical connector pin-outs, sensor sensitivities, and the like. By way of illustration, although an example ammonia sensor may have six electrical connectors or pins (e.g., TGS 826) and an example tri-methylamine sensor (e.g., TGS 2603) may have four electrical connectors or pins, similar data acquisition and monitoring schemes may be implemented according to the teachings herein. In one implementation, example sensor interface wiring and signal interconnect wiring may comprise standard AMP connectors, RJ-45 connectors, CAT-5 connectors, etc., although some arrangements may involve wireless connectivity. Further, bus technologies such as Peripheral Component Interconnect (PCI), PCI Express, PCI eXtensions for Instrumentation (PXI), PXI Express, Ethernet, etc. may also be employed in some DAQ arrangements. Analog voltage data from the sensors may be processed by the DAQ and provided to a computer-implemented monitoring system wherein suitable program logic or instructions may be executed by a processor for characterizing the amounts of the byproducts present in an exhaust stream. Depending on the processing flows, electrical characteristics of the sensors and tooling conditions, etc., different thresholds may be established for different byproducts, which may be used in determining whether or not a particular byproduct is present in a sufficient quantity indicative of a satisfactory HMDS reaction process. If low amounts of a benchmark byproduct are detected, appropriate containment and corrective actions may be undertaken with respect to the WIP wafers.

Although ammonia and tri-methylamine sensor manifold assemblies have been described in detail hereinabove, it should be appreciated that various other sensors may be deployed in additional and/or alternative arrangements wherein suitable modular sensor manifold assemblies may be fabricated in accordance with the teachings herein. For example, organic solvent sensors, high VOC sensors, etc., may be deployed in combination with or independent from ammonia and tri-methylamine sensors in an example process flow for sensing, detecting, measuring appropriate benchmark byproducts and determining and/or identifying appropriate control actions regarding the WIP wafers. Further, depending on the form factors of the sensors deployed in an arrangement, example sensor manifold assemblies may include housing blocks and/or cover plates of various sizes, shapes, form factors, and the like, wherein the various apertures, sensor receptacles, and/or input and output orifices, may be designed with appropriate shapes, sizes, etc., for accommodating suitable sealing arrangements.

Additionally, because process recipes can change significantly within a fabrication facility or across different facilities, e.g., depending on tool type and/or processing requirements, process thresholds for the detected/monitored byproducts of an exhaust stream can also vary considerably. In some process flows, a satisfactory HMDS run may generate 30-50 ppm of ammonia and 10-15 ppm of tri-methylamine as byproducts. In one implementation, a process "failure" point or threshold may be established when a 50% or more reduction in these values is detected. On other tool types running different recipes for HMDS application, satisfactory runs may generate lower amounts of ammonia and tri-methylamine, e.g., 15-20 ppm of ammonia and 5-10 ppm of tri-methylamine. In such tooling conditions, actionable processing thresholds may be established when the monitored byproducts fall below 25% of expected output.

Because example embodiments of an exhaust monitoring system of the present disclosure may be implemented with substantial flexibility, one implementation may involve characterizing and modeling the behavior of an HMDS reaction chamber tool to determine a current satisfactory operating point (i.e., "finger printing") and then setting appropriate process thresholds or limits around or relative to the operating point(s) (e.g., in terms of absolute or relative ranges, percentages, etc.) for different byproducts accordingly. Such thresholds may also depend on the sensor sensitivities in some arrangements. Different thresholds may therefore be implemented for the same benchmark byproducts depending on the processing/tool conditions.

Figure 13A:
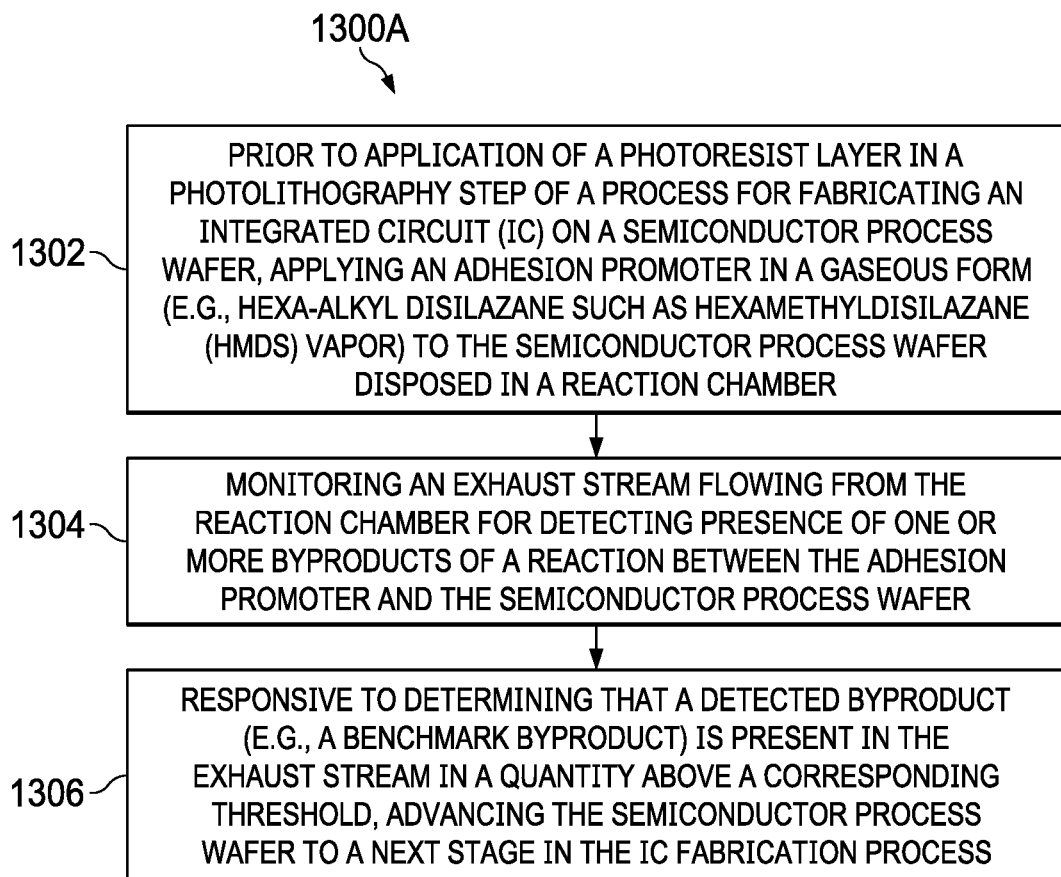
FIGS. 13A and 13B depict an example method according to an implementation of the disclosure.
Figure 13B:
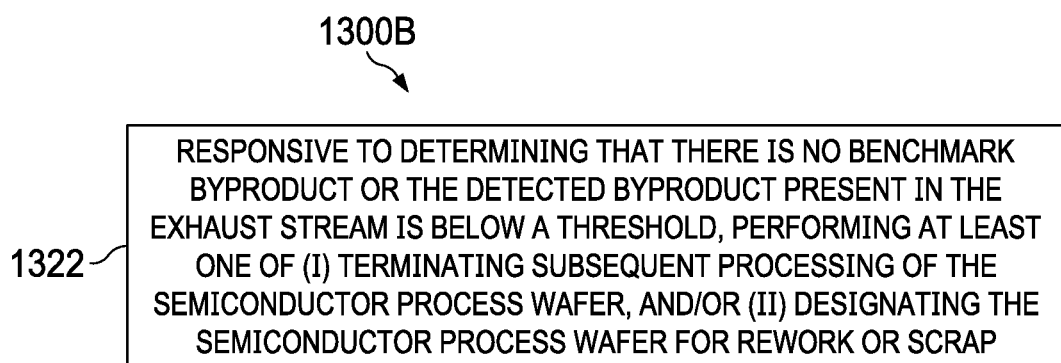

FIGS. 13A and 13B depict flowcharts relating to an example method according to an implementation of the disclosure. Process flow 1300A may commence with applying an adhesion promoter in a gaseous form (e.g., hexa-alkyl disilazane such as hexamethyldisilazane (HMDS) vapor) to a semiconductor process wafer disposed in a reaction chamber, e.g., prior to application of a photoresist layer in a photolithography step of a process flow used for fabricating an IC in or over the semiconductor process wafer, as set forth at block 1302. At block 1304, an exhaust stream flowing from the reaction chamber is monitored for detecting the presence of one or more byproducts (e.g., benchmark byproducts) of a reaction between the adhesion promoter, semiconductor process wafer and associated surface layers. Responsive to determining that a detected byproduct is present in the exhaust stream in a quantity above a corresponding threshold, the semiconductor process wafer is advanced to a next stage in the IC fabrication process, as set forth at block 1306, which may involve application of a suitable PR material using any known or heretofore unknown techniques and process recipes depending on the layer to be patterned, spectral characteristics of the light/radiation used in photolithography for exposure (e.g., 436 nm ("g-line"), 405 nm ("h-line") and 365 nm ("i-line"), X-rays, etc.), and the like. Process flow 1300B involves a variation wherein additional and/or alternative actions may be undertaken responsive to determining that a benchmark byproduct is absent in the exhaust stream or is present below a corresponding threshold. For example, a process flow may involve performing, without limitation, at least one of (i) terminating subsequent processing of the semiconductor wafer (e.g., the semiconductor process wafer is not advanced to PR application), and/or (ii) designating the semiconductor process wafer for rework or scrap, as set forth at block 1322.

As noted previously, an example IC fabrication flow may include a number of photolithography steps that may take place during various stages of semiconductor wafer processing. Accordingly, suitable PR adhesion promoter tooling and associated exhaust monitoring may be deployed at one or more stages of the fabrication flow according to example embodiments of the present disclosure. In one implementation, each adhesion promoter tooling and associated exhaust monitoring stage may involve detection of particular benchmark byproducts based on specific process recipes for achieving appropriate surface treatments, specific sensor types and corresponding manifold assemblies, as well as respective reaction chamber operating points and applicable thresholds. Additionally, an exhaust monitoring scheme may also vary depending on the wafer substrate materials (e.g., Si, SiC, SiGe, GaAs or an organic semiconductor material, etc.), surface layer materials and compositions, adhesion promoter materials (e.g., HMDS, non-HMDS, etc.), and the like. Example embodiments therefore provide an adaptable system for monitoring exhaust gases in a robust yet flexible manner, which may be practiced in a number of fabrication environments.

Further, example embodiments may be deployed at various stages of an IC fabrication flow including FEOL and BEOL stages, depending on how many conducting and insulating layers (e.g., polysilicon layers, metal layers, dielectric layers, etc.) are patterned and added in an IC chip. In general, FEOL process flow may be considered as the first portion of IC fabrication where the individual devices (e.g., transistors, capacitors, resistors, etc.) are patterned in a semiconductor wafer. FEOL generally includes IC processing up to but not including the deposition of metal interconnect layers. For an example CMOS process, by way of illustration, FEOL may contain all fabrication steps needed to form fully isolated CMOS elements, which may include wafer preparation, shallow trench isolation, n-well/p-well formation, gate formation, and source/drain formation. In an example fabrication flow involving complex IC devices, a CMOS wafer may go through a photolithographic cycle as many as 10-50 times.

BEOL process flow comprises the second portion of IC fabrication where the individual devices get interconnected with one or more layers of wiring (referred to as metallization layers). BEOL generally begins when the first metal layer is deposited on the patterned wafer from FEOL (e.g., with isolated devices) that has undergone silicidation and pre-metal dielectric deposition. An interconnect metal layer (e.g., a copper or tungsten layer) may be patterned according to a photolithographic cycle that is preceded by an AP application and exhaust monitoring process according to one implementation of the present disclosure. As BEOL may include several inter-metal dielectric layers separating respective metal layers and formation of inter-metal vias, multiple photolithographic cycles may be implemented in an example BEOL flow. Accordingly, appropriate AP tooling and associated exhaust monitoring schemes may also be deployed at one or several metal levels of a BEOL process flow in some implementations.

Example implementations herein advantageously allow direct monitoring of an HMDS reaction process based on the detection of designated byproducts rather than monitoring intake gases (i.e., carrier gases) that only provides an indirect and often inadequate assessment of the reaction process. Because example implementations provide the ability to detect potential failures in the PR adhesion process in real time, immediate notification and correction of the failures may be undertaken, thereby preventing large amounts of defect product and/or scrap events from occurring.

Although various implementations have been shown and described in detail, the claims are not limited to any particular implementation or example. None of the above Detailed Description should be read as implying that any particular component, element, step, act, or function is essential such that it must be included in the scope of the claims. Where the phrases such as "at least one of A and B" or phrases of similar import are recited or described, such a phrase should be understood to mean "only A, only B, or both A and B." Reference to an element in the singular is not intended to mean "one and only one" unless explicitly so stated, but rather "one or more." All structural and functional equivalents to the elements of the above-described implementations that are known to those of ordinary skill in the art are expressly incorporated herein by reference and are intended to be encompassed by the present claims.

It should further be understood that the order or sequence of the acts, steps, functions, components or blocks illustrated in any of the flowcharts depicted in the drawing Figures of the present disclosure may be modified, altered, replaced, customized or otherwise rearranged within a particular flowchart, including deletion or omission of a particular act, step, function, component or block. Moreover, the acts, steps, functions, components or blocks illustrated in a particular flowchart may be inter-mixed or otherwise inter-arranged or rearranged with the acts, steps, functions, components or blocks illustrated in another flowchart in order to effectuate additional variations, modifications and configurations with respect to one or more processes for purposes of the present patent disclosure. Accordingly, those skilled in the art will recognize that the example implementations described herein can be practiced with various modifications and alterations within the spirit and scope of the claims appended below.

What is claimed is:

1. A method of fabricating an integrated circuit (IC), the method comprising:
   prior to application of a photoresist layer in a photolithography step used in fabricating the integrated circuit on a semiconductor process wafer, applying an adhesion promoter in a gaseous form to the semiconductor process wafer disposed in a reaction chamber;
   monitoring an exhaust stream flowing from the reaction chamber for detecting presence of one or more byproducts of a reaction between the adhesion promoter and the semiconductor process wafer; and
   responsive to determining that a detected byproduct is present in the exhaust stream in a quantity above a corresponding threshold, advancing the semiconductor process wafer to a next stage in IC fabrication.

2. The method as recited in claim 1, further comprising, responsive to determining that a benchmark byproduct is absent in the exhaust stream or present below the corresponding threshold, performing at least one of (i) terminating subsequent processing of the semiconductor process wafer, and (ii) designating the semiconductor process wafer for rework.

3. The method as recited in claim 1, wherein the adhesion promoter comprises a hexamethyldisilazane (HMDS) vapor carried in a nitrogen carrier gas that is supplied as an inflow into the reaction chamber.

4. The method as recited in claim 3, further comprising heating the semiconductor process wafer at a temperature ranging approximately between 70° C. and 150° C. for about 5 to 30 seconds.

5. The method as recited in claim 4, wherein the one or more byproducts comprise at least one of ammonia, tri-methylamine and one or more volatile organic compounds (VOCs).

6. The method as recited in claim 5, wherein the exhaust stream is monitored by an ammonia sensor to detect the presence of ammonia in the exhaust stream.

7. The method as recited in claim 5, wherein the exhaust stream is monitored by a tri-methylamine sensor to detect the presence of tri-methylamine in the exhaust stream.

8. The method as recited in claim 5, wherein the exhaust stream is monitored by a VOC sensor to detect the presence of a VOC in the exhaust stream.

9. A method of fabricating an integrated circuit (IC), comprising:

exposing a semiconductor substrate to an adhesion promoter in a reaction chamber;

monitoring an exhaust stream flowing from the reaction chamber; and in the event that a reaction byproduct of a reaction between the semiconductor substrate and the adhesion promoter is detected, advancing the semiconductor substrate to a later stage of fabricating the IC.

10. The method as recited in claim 9, wherein the adhesion promoter comprises a hexamethyldisilazane (HMDS).

11. The method as recited in claim 9, further comprising heating the semiconductor substrate at a temperature ranging approximately between 70° C. and 150° C. for about 5 to 30 seconds while exposed to the adhesion promoter.

12. The method as recited in claim 9, wherein the reaction byproduct comprises at least one of ammonia, tri-methylamine and one or more volatile organic compounds (VOCs).

13. The method as recited in claim 9, further comprising, prior to exposing the semiconductor substrate to the adhesion promoter, exposing the semiconductor substrate to vacuum.

14. The method as recited in claim 9, wherein the exhaust stream is monitored by a tri-methylamine sensor to detect presence of tri-methylamine in the exhaust stream.

15. The method as recited in claim 9, wherein the exhaust stream is monitored by an ammonia sensor to detect presence of ammonia in the exhaust stream.

16. The method as recited in claim 9, wherein the later stage includes forming a photoresist layer over the semiconductor substrate.

17. A method of manufacturing an integrated circuit (IC), comprising:

directing production wafer into a reaction chamber;

exposing the production wafer to hexamethyldisilazane (HMDS) in the reaction chamber;

directing the production wafer to a photoresist coating process only on the condition that a reaction byproduct of a reaction between the production wafer and the HMDS is detected.

18. The method as recited in claim 17, wherein the reaction byproduct comprises ammonia.

19. The method as recited in claim 17, wherein presence of the reaction byproduct is determined by a sensor exposed to a gaseous exhaust stream from the reaction chamber.

20. The method as recited in claim 17, further comprising pattering a photoresist layer produced by the photoresist coating process with a pattern representing a material layer of the integrated circuit.

* * * * *